United States Patent
Luca et al.

(10) Patent No.: US 12,054,834 B2
(45) Date of Patent: Aug. 6, 2024

(54) METHODS FOR CHEMICAL DEGRADATION OF POLYESTER POLYMERS

(71) Applicant: The Regents of the University of Colorado, a body corporate, Denver, CO (US)

(72) Inventors: Oana Luca, Denver, CO (US); Tessa Myren, Denver, CO (US); Chloe Huntzinger, Denver, CO (US); Taylor A Stinson, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 17/538,001

(22) Filed: Nov. 30, 2021

(65) Prior Publication Data
US 2022/0170167 A1    Jun. 2, 2022

Related U.S. Application Data

(60) Provisional application No. 63/119,159, filed on Nov. 30, 2020.

(51) Int. Cl.
| | |
|---|---|
| *C25B 3/07* | (2021.01) |
| *C07C 29/00* | (2006.01) |
| *C07C 51/09* | (2006.01) |
| *C25B 3/20* | (2021.01) |
| *C25B 9/65* | (2021.01) |

(52) U.S. Cl.
CPC ............... *C25B 3/07* (2021.01); *C07C 29/00* (2013.01); *C07C 51/09* (2013.01); *C25B 3/20* (2021.01); *C25B 9/65* (2021.01)

(58) Field of Classification Search
None
See application file for complete search history.

(56) References Cited

U.S. PATENT DOCUMENTS

2017/0342219 A1* 11/2017 Stahl ................... C08H 6/00

FOREIGN PATENT DOCUMENTS

JP         2004250544 A   *  9/2004

OTHER PUBLICATIONS

Kamata, JP 2004250544 A, machine translation (Year: 2004).*
Advancing Sustainable Materials Management: 2016 and 2017 Tables and Figures; U.S. Environmental Protection Agency: Washington, DC, USA, 2019.
Advancing Sustainable Materials Management: 2018 Fact Sheet, US EPA Dec. 2020. 25 pages.
Al-Salem, S.; Lettieri, P.; Baeyens, J. Recycling and recovery routes of plastic solid waste (PSW): A review. Waste Manag. 2009, 29, 2625-2643.
Aoki, Y., Li, L., Amari, T., Nishimura, K., & Arashiro, Y. (1999). Dynamic Mechanical Properties of Poly(ethylene terephthalate)/Poly(ethylene 2,6-naphthalate) Blends. Macromolecules, 32(6), 1923-1929. doi: 10.1021/ma981657w.
Arai, Risa, et al. "Reaction kinetics of hydrothermal depolymerization of poly (ethylene naphthalate), poly (ethylene terephthalate), and polycarbonate with aqueous ammonia solution." Chemical engineering science 65.1 (2010): 36-41.
Arena, U.; Mastellone, M.L. Particle agglomeration during energy recovery from plastic wastes by means of fluidized bed reactors; Univ. Federico II of Naples: Napoli, Italy, 1999.
Awaja, F.; Pavel, D. Recycling of PET. Eur. Polym. J. 2005, 41, 1453-1477.
Bei, Ke, et al. "Depolymerization of poly (ethylene naphthalate) in fused silica capillary reactor and autoclave reactor from 240 to 280 C in subcritical water." Polymer Engineering & Science 57.12 (2017): 1382-1388.
Britt, et al., Goldman and J. Guzman, Report of the Basic Energy Sciences Roundtable on Chemical Upcycling of Polymers, USDOE Office of Science (SC)(United States), 2019.
Carta, D.; Cao, G.; D'Angeli, C. Chemical recycling of poly (ethylene terephthalate)(PET) by hydrolysis and glycolysis. Environ. Sci. Pollut. Res. 2003, 10, 390-394.
Chang, S., Sheu, M.-F., & Chen, S.-M. (1983). Solid-state polymerization of poly(ethylene terephthalate). Journal of Applied Polymer Science, 28(10), 3289-3300. doi:10.1002/app.1983.070281023.
Chen, Chin-Wen, et al. "Crystal Structure and Tensile Fracture Morphology of Poly (ethylene terephthalate)-co-poly (ethylene 2, 6-naphthalate) Block Copolyesters and Fibers." Industrial & Engineering Chemistry Research 59.41 (2020): 18717-18725.
Clark, D.E. Peroxides and peroxide-forming compounds. Chem. Health Saf. 2001, 8,12-22.
Conway, B.; Dzieciuch, M. New Approaches to the Study of Electrochemical Decarboxylation and the Kolbe Reaction: Part I. The Model Reaction with 5 Formate. Can. J. Chem. 1963, 41, 21-37.
Conway, B.; Dzieciuch, M. New Approaches to the Study of Electrochemical Decarboxylation and the Kolbe Reaction: Part II. The Model Reaction with Trifluoroacetate and Comparisons with Aqueous Solution Behavior. Can. J. Chem. 1963, 41, 38-54.
Cruz, S.A.; Zanin, M. PET recycling: Evaluation of the solid state polymerization process. J. Appl 2006, 99, 2117-2123.
Doina Dimonie, R.S.; Pop, S.; Fierascu, I.; Fierascu, R.; Petra, C.; Zaharia, C.; Patrache, M. Overview on Mechanic Recycling by Chain Extension of POSTC-PET Bottles. In Material Recycling: Trends and Perspectives; Achilias, D.S., Ed.; InTech: Rijeka, Croatia, 2012.
Emissions of Greenhouse Gases in the United States 2006 (DOE/EIA-0573); U.S. Energy Information Administration: Washington, DC, USA, 2006.

(Continued)

*Primary Examiner* — Wojciech Haske
(74) *Attorney, Agent, or Firm* — Meunier Carlin & Curfman LLC (57) ABSTRACT

The present disclosure provides methods for the chemical degradation of polymers, in particular to methods for the degradation of polyesters by electrochemical processes.

16 Claims, 1 Drawing Sheet

(56) References Cited

OTHER PUBLICATIONS

Fitaroni, L.B.; De Oliveira, É.C.; Marcomini, A.L.; Paranhos, C.M.; Freitas, F.L.; Cruz, S.A. Reprocessing and Solid State Polymerization on Contaminated Post-consumer PET: Thermal and Crystallization Behavior. J. Polym. Environ. 2020, 28, 91-99.

Fujisawa, S.; Kadoma, Y.; Yokoe, I. Radical-scavenging activity of butylated hydroxytoluene (BHT) and its metabolites. Chem. Phys. Lip. 2004, 130, 189-195.

Fukushima, K.; Coulembier, O.; Lecuyer, J. M.; Almegren, H. A.; Alabdulrahman, A. M.; Alsewailem, F. D.; Mcneil, M. A.; Dubois, P.; Waymouth, R. M.; Horn, H. W. Organocatalytic depolymerization of poly (ethylene terephthalate). Journal of Polymer Science Part A: Polymer Chemistry 2011, 49, 1273-1281.

George, N.; Kurian, T. Recent Developments in the Chemical Recycling of Postconsumer Poly(ethylene terephthalate) Waste. Ind. Eng. Chem. Res. 2014, 53, 14185-14198.

Guart, A.; Bono-Blay, F.; Borrell, A.; Lacorte, S. Migration of plasticizersphthalates, bisphenol A and alkylphenols from plastic containers and evaluation of risk. Food Addit. Contam. A 2011, 28, 676-685.

Hodge, Philip, et al. "Cyclo-depolymerisation of poly (ethylene naphthalene-2, 6-dicarboxylate) and ring-opening polymerisations of the cyclic oligomers obtained." Journal of Materials Chemistry 10.7 (2000): 1533-1537.

Hu, L.-C.; Oku, A.; Yamada, E.; Tomari, K. Alkali-decomposition of poly (ethylene terephthalate) in mixed media of nonaqueous alcohol and ether. Study on recycling of poly (ethylene terephthalate). Polym. J. 1997, 29, 708-712.

Institute, F. PET-recyclate from post-consumer waste. Available online: https://www.ivv.fraunhofer.de/en/recycling-environment/packaging-recycling/petrecycling. html (accessed on Jun. 1, 2020).

Jamshidian, Majid, et al. "Poly-lactic acid: production, applications, nanocomposites, and release studies." Comprehensive reviews in food science and food safety 9.5 (2010): 552-571.

Jehanno, C.; Pérez-Madrigal, M. M.; Demarteau, J.; Sardon, H.; Dove, A. P. Organocatalysis for depolymerisation. Polymer Chemistry 2019, 10, 172-186.

Jia, H., Zhang, M., Weng, Y., Zhao, Y., Li, C., & Kanwal, A. (2021). Degradation of poly(butylene adipate-co-terephthalate) by *Stenotrophomonas* sp. YCJ1 isolated from farmland soil. Journal of Environmental Sciences, 103, 50-58.

Jie, H., Ke, H., Wenjie, Q., & Zibin, Z. (2006). Process analysis of depolymerization polybutylene terephthalate in supercritical methanol. Polymer Degradation and Stability, 91(10), 2527-2531. doi:10.1016/j.polymdegradstab.2006.01.014.

Kaplan, D.L. Introduction to biopolymers from renewable resources. In Biopolymers from renewable resources, Springer: New York, 1998; pp. 1-29.

Kappe, C.O.; Dallinger, D. The impact of microwave synthesis on drug discovery. Nat. Rev. Drug Discov. 2006, 5, 51-63.

Kuczenski, B.; Geyer, R. Material flow analysis of polyethylene terephthalate in the US, 1996-2007. Resour. Conserv. Recy. 2010, 54, 1161-1169.

Kuczenski, Brandon, and Roland Geyer. "Material flow analysis of polyethylene terephthalate in the US, 1996-2007." Resources, Conservation and Recycling 54.12 (2010): 1161-1169.

Luca, O.R.; Blakemore, J.D.; Konezny, S.J.; Praetorius, J.M.; Schmeier, T.J.; Hunsinger, G.B.; Batista, V.S.; Brudvig, G.W.; Hazari, N.; Crabtree, R.H. Organometallic Ni pincer complexes for the electrocatalytic production of hydrogen. Inorg. Chem. 2012, 51, 8704-8709.

Luca, O.R.; Konezny, S.J.; Blakemore, J.D.; Colosi, D.M.; Saha, S.; Brudvig, G.W.; Batista, V.S.; Crabtree, R.H. A tridentate Ni pincer for aqueous electrocatalytic hydrogen production. New J. Chem. 2012, 36, 1149-1152.

Marsh, Kenneth, and Betty Bugusu. "Food packaging—roles, materials, and environmental issues." Journal of food science 72.3 (2007): R39-R55.

Mast, Z.J.; Myren, T.H.; Huntzinger, C.G.; Stinson, T.A.; Kharbouch, R.M.; Almanza, E.M.; Zygmont, S.E.; Miecznikowski, J.R.; Luca, O.R. Cu I SNS triazole and imidazole pincers as electrocatalyst precursors for the production of solar fuels. Inorg. Chem. Front. 2020, 7, 1012-1015.

Mishra, S.; Goje, A.; Zope, V. Chemical recycling, kinetics, and thermodynamics of poly (ethylene terephthalate) (PET) waste powder by nitric acid hydrolysis. Polym. React. Eng. 2003, 11, 79-99.

Myren, T.H.; Alherz, A.; Thurston, J.R.; Stinson, T.A.; Huntzinger, C.G.; Musgrave, C.B.; Luca, O.R. Mn-Based Molecular Catalysts for the Electrocatalytic Disproportionation of $CO_2$ into CO and $CO_3$ 2-. ACS Catal. 2020, 10, 1961-1968.

Myren, T.H.; Lilio, A.M.; Huntzinger, C.G.; Horstman, J.W.; Stinson, T.A.; Donadt, T.B.; Moore, C.; Lama, B.; Funke, H.H.; Luca, O.R. Manganese N-heterocyclic carbene pincers for the electrocatalytic reduction of carbon dioxide. Organometallics 2018, 38, 1248-1253.

Myren, Tessa HT, et al. "Chemical and electrochemical recycling of end-use poly (ethylene terephthalate)(PET) plastics in batch, microwave and electrochemical reactors." Molecules 25.12 (2020): 2742.

Paszun, D.; Spychaj, T. Chemical recycling of poly (ethylene terephthalate). Ind. Eng. Chem. Res. 1997, 36, 1373-1383.

Petersen, Haley A., et al. "Electrochemical methods for materials recycling." Materials Advances 2.4 (2021): 1113-1138.

Ragaert, K.; Delva, L.; Van Geem, K. Mechanical and chemical recycling of solid plastic waste. Waste Manag. 2017, 69, 24-58.

Rastin, H.; Ahmadi, Z.; Pakdel, A.S.; Saeb, M.R.; Abbasian, Y.; Liravi, M.; Eslahi, A. A physicochemical route for compensation of molecular weight loss during recycling of poly(ethylene terephthalate). J. Vinyl Addit. Technol. 2016, 22, 387-395.

Roger Lin, Electrochemical Reactors for $CO_2$ Conversion, Catalysts 2020, 10, 473; doi:10.3390/catal10050473.

Sato, Osamu, Kunio Arai, and Masayuki Shirai. "Decomposition behavior of poly (ethylene-2, 6-naphthalene dicarboxylate) in high temperature water." Fluid phase equilibria 228 (2005): 523-525.

Sheehan, R.J. Terephthalic Acid, Dimethyl Terephthalate, and Isophthalic Acid. In Ullmann's Encyclopedia of Industrial Chemistry, John Wiley & Sons: Hoboken, NJ, 2011.

Shen, Zhiyuan, et al. "A study on mediating the crystallization behavior of PBT through intermolecular hydrogen-bonding." RSC advances 6.21 (2016): 17510-17518.

Siddiqui, M.N.; Achilias, D.S.; Redhwi, H.H.; Bikiaris, D.N.; Katsogiannis, K.A.G.; Karayannidis, G.P. Hydrolytic depolymerization of PET in a microwave reactor. Macromol. Mater. Eng. 2010, 295, 575-584.

Singh, N., Hui, D., Singh, R., Ahuja, I. P. S., Feo, L., & Fraternali, F. (2017). Recycling of plastic solid waste: A state of art review and future applications. Composites Part B: Engineering, 115, 409-422. doi:10.1016/j.compositesb.2016.09.

Tabone, M.D.; Cregg, J.J.; Beckman, E.J.; Landis, A.E. Sustainability metrics: life cycle assessment and green design in polymers. Environ. Sci. Technol. 2010, 44, 8264-8269.

Thiounn, T.; Smith, R.C. Advances and approaches for chemical recycling of plastic waste. J. Polym. Sci. 2020, 58, 1347-1364.

Wang, et al., Are Ionic Liquids Chemically Stable? Chem. Rev. 2017, 117, 7113-7131, 10.1021/acs.chemrev.6b00594.

Yamamoto, Yumiko, Hiromichi Hoshina, and Harumi Sato. "Differences in intermolecular interactions and flexibility between poly (ethylene terephthalate) and poly (butylene terephthalate) studied by far-infrared/terahertz and low-frequency Raman spectroscopy." Macromolecules 54.2 (2021): 1052-1062.

Yamaye, Makoto, et al. "Chemical recycling of polyesters. One-pot-two-step conversion of poly (ethylene 2, 6-naphthalenedicarboxylate) and poly (tetramethylene terephthalate), producing the corresponding hydroxamic acids and hydrazides." Polymer degradation and stability 91.9 (2006): 2014-2021.

Yin, Jiajie, et al. "Rapid crystallization of poly (ethylene 2, 6-naphthalate) via aryl amide derivatives." Polymer-Plastics Technology and Materials 59.16 (2020): 1842-1853.

Yoshioka, T.; Sato, T.; Okuwaki, A. Hydrolysis of waste PET by sulfuric acid at 150° C. for a chemical recycling. J. Appl. Polym. Sci. 1994, 52, 1353-1355.

* cited by examiner

METHODS FOR CHEMICAL DEGRADATION OF POLYESTER POLYMERS

CROSS-REFERENCE TO RELATED APPLICATIONS

This application claims the benefit of priority to U.S. Provisional Application No. 63/119,159, filed Nov. 30, 2020, the disclosure of which is incorporated herein by reference in its entirety.

TECHNICAL FIELD

This disclosure relates to methods for the degradation of polymers, and more particularly to electrochemical and related methods for the degradation of polyester polymers.

BACKGROUND

Figure 1A:
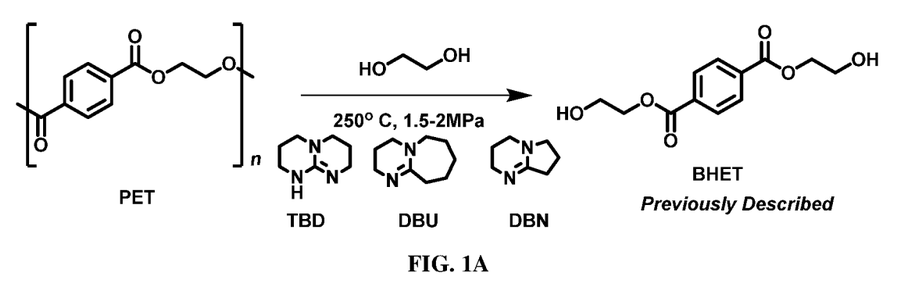
FIGS. 1A, 1B, 1C, and 1D are schemes showing previously described representative chemical depolymerization methods for depolymerization of poly(ethylene terephthalate) (PET) such as (FIG. 1A) glycolysis as described previously (FIG. 1B) alcoholysis as described previously (FIG. 1C) aminolysis as described previously and (FIG. 1D) the chemical depolymerization methods of the present disclosure using batch, microwave, and electrochemical processes.
Figure 1B:
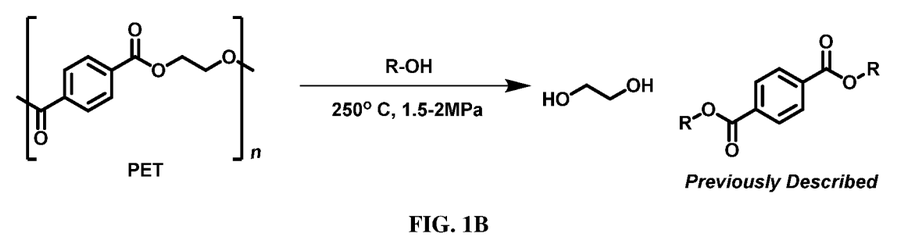
Figure 1C:
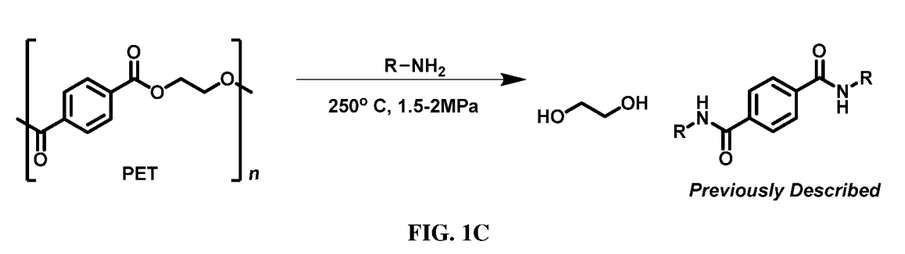
Figure 1D:
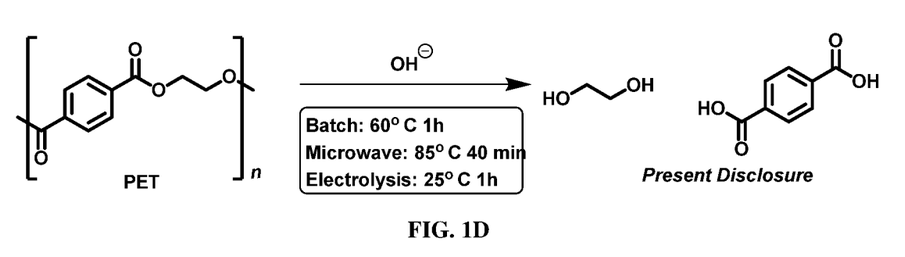

The rate at which municipal solid waste is generated and landfilled directly correlates to the use and disposal of plastic waste. An estimated 35.4 million tons of plastic were produced in 2017 in the United States. Of the plastic waste produced in the U.S., 5.01 million tons were poly(ethylene terephthalate) (PET) (*Advancing Sustainable Materials Management: 2016 and 2017 Tables and Figures*; U.S. Environmental Protection Agency: Washington, DC, USA, 2019). While PET is generally the most recovered plastic, the amount of waste PET that is recycled is still low, especially given the scale of use. This leads to an increased volume of landfills as discarded plastic is not biodegradable which contributes negatively to greenhouse gas emissions, and has detrimental effects on the world's ecosystems, most specifically on marine life (Kuczenski, B.; Geyer, R. Material flow analysis of polyethylene terephthalate in the US, 1996-2007. *Resour. Conserv. Recy.* 2010, 54, 1161-1169; *Emissions of Greenhouse Gases in the United States* 2006 (*DOE/EIA*-0573); U.S. Energy Information Administration: Washington, DC, USA, 2006; and Seinfeld, J. H.; Pandis, S. N. *Atmospheric chemistry and physics: from air pollution to climate change*, 3rd ed.; John Wiley & Sons: Hoboken, NJ, 2016). The most commonly reported reason for lack of recycling is the inaccessibility to recycling resources. A life cycle analysis (Tabone, M. D.; Cregg, J. J.; Beckman, E. J.; Landis, A. E. Sustainability metrics: life cycle assessment and green design in polymers. *Environ. Sci. Technol.* 2010, 44, 8264-8269) based on the twelve principles of green chemistry (Anastas, P. T.; Warner, J. C. Green Chemistry: Theory and Practice. Oxford University Press: Oxford, England, 1998) by Landis and coworkers has highlighted the low biodegradability, high ecotoxicity and overall environmental impact of PET, despite extensive efforts in its recovery and recycling. While new biodegradable polymers become available (Kaplan, D. L. Introduction to biopolymers from renewable resources. In *Biopolymers from renewable resources*, Springer: New York, 1998; pp. 1-29), there is continued use and accumulation of PET that needs to be addressed. As such, improved methods for its reuse through recycling are sought. Recycling of PET can be divided into four main practices: primary, quaternary, mechanical, and chemical. Primary recycling involves recycling of PET before it reaches the hands of the consumer. This process re-extrudes the plastic material and requires that the plastic be clean and separated, such that primary recycling feedstock often comes directly from the plastic manufacturing plant (Ragaert, K.; Delva, L.; Van Geem, K. Mechanical and chemical recycling of solid plastic waste. *Waste Manag.* 2017, 69, 24-58). The added need for separation significantly impacts the cost of the method. Mechanical recycling implements heat and mechanical force to break down the polymer and then incorporate it into another useable material without changing the chemical identity of the polymer (Thiounn, T.; Smith, R. C. Advances and approaches for chemical recycling of plastic waste. *J. Polym. Sci.* 2020, 58, 1347-1364). Mechanical recycling is still a major recycling process, despite causing a decrease in molecular weights, due to its simplicity and low investment costs (Awaja, F.; Pavel, D. Recycling of PET. *Eur. Polym. J.* 2005, 41, 1453-1477). Solid-state polycondensation (SSP) is a physical modification process used in PET production to increase the molecular weight and quality of the polymer (Chang, S.; Sheu, M.-F.; Chen, S.-M. Solid-state polymerization of poly(ethylene terephthalate). *J. Appl* 1983, 28, 3289-3300). It is used following mechanical methods to make "bottle to bottle" recycling possible (Rastin, H.; Ahmadi, Z.; Pakdel, A. S.; Saeb, M. R.; Abbasian, Y.; Liravi, M.; Eslahi, A. A physicochemical route for compensation of molecular weight loss during recycling of poly(ethylene terephthalate). *J. Vinyl Addit. Technol.* 2016, 22, 387-395). However, it is affected by contaminants and requires long reaction times and expensive control devices (Cruz, S. A.; Zanin, M. PET recycling: Evaluation of the solid state polymerization process. *J. Appl* 2006, 99, 2117-2123; Fitaroni, L. B.; De Oliveira, É. C.; Marcomini, A. L.; Paranhos, C. M.; Freitas, F. L.; Cruz, S. A. Reprocessing and Solid State Polymerization on Contaminated Post-consumer PET: Thermal and Crystallization Behavior. *J. Polym. Environ.* 2020, 28, 91-99; and Doina Dimonie, R. S.; Pop, S.; Fierascu, I.; Fierascu, R.; Petra, C.; Zaharia, C.; Patrache, M. Overview on Mechanic Recycling by Chain Extension of POSTC-PET Bottles. In *Material Recycling: Trends and Perspectives*; Achilias, D. S., Ed.; InTech: Rijeka, Croatia, 2012). Quaternary recycling recovers energy from plastic by incineration (Al-Salem, S.; Lettieri, P.; Baeyens, J. Recycling and recovery routes of plastic solid waste (PSW): A review. *Waste Manag.* 2009, 29, 2625-2643). This recycling method is process-intensive and produces greenhouse gases. While it is beneficial for multiple recycling methods to be implemented, the majority of the recycling performed on scale is not sustainable due to intensive use of resources and low-value recovery. In contrast to primary, quaternary and mechanical processes, chemical recycling is a sustainable recycling option. Chemical recycling leads to the breakdown of the polymer esters into monomers or other smaller components, thus changing the chemical identity of the starting material, which can then be used to reform the polymer or produce valuable chemicals. The ultimate goal of chemical recycling—and the focus of this work—is to recover monomer materials to use as a feedstock for the production of new plastics and chemicals (Arena, U.; Mastellone, M. L. *Particle agglomeration during energy recovery from plastic wastes by means of fluidized bed reactors*; Univ. Federico II of Naples: Napoli, Italy, 1999). The Fraunhofer Institute in Germany is working on the upcycling of PET using chemical methods which do not require prior separation from other consumer waste (Institute, F. PET-recyclate from post-consumer waste. Available online: https://www.ivv.fraunhofer.de/en/recycling-environment/packaging-recycling/pet-recycling.html, accessed on 1 Jun. 2020). The chemical recycling of PET can be further broken down into two main methods: glycolysis and hydrolysis (or alcoholysis). Glycolysis involves the insertion of ethylene glycol or its derivatives into the PET chain to produce a monomer of the PET polymer, bis-(hydroxyethyl) terephthalate, as shown in FIG. 1A (Carta, D.; Cao, G.; D'Angeli, C. Chemical recycling of poly (ethylene terephthalate)(PET) by hydrolysis and glycolysis. *Environ. Sci. Pollut. Res.* 2003, 10, 390-394). The conditions for this reaction often require high temperatures from 180° C. to 240° C. and high pressures (Paszun, D.; Spychaj, T. Chemical recycling of poly (ethylene terephthalate). *Ind. Eng. Chem. Res.* 1997, 36, 1373-1383). Organic bases such as 1,5,7-triazabicyclo [4.4.0]dec-5-ene (TBD), 1,8-diazabicyclo[5.4.0]undec-7-ene (DBU), and 1,5-diazabicyclo[4.3.0]non-5-ene (DBN) can be used for the depolymerization of PET to monomers that can then be used for repolymerization (Jehanno, C.; Pérez-Madrigal, M. M.; Demarteau, J.; Sardon, H.; Dove, A. P. Organocatalysis for depolymerisation. *Polymer Chemistry* 2019, 10, 172-186). Glycolysis is the oldest chemical PET recycling method and has been used commercially for more than 40 years (George, N.; Kurian, T. Recent Developments in the Chemical Recycling of Postconsumer Poly(ethylene terephthalate) Waste. *Ind. Eng. Chem. Res.* 2014, 53, 14185-14198). Glycolysis uses TBD in an excess of ethylene glycol at 190° C. to convert PET to bis(2-hydroxyethyl)terephthalate (BHET), a monomer for polymerization of high-quality PET, in a 78% yield (Fukushima, K.; Coulembier, O.; Lecuyer, J. M.; Almegren, H. A.; Alabdulrahman, A. M.; Alsewailem, F. D.; Mcneil, M. A.; Dubois, P.; Waymouth, R. M.; Horn, H. W. Organocatalytic depolymerization of poly (ethylene terephthalate). *Journal of Polymer Science Part A: Polymer Chemistry* 2011, 49, 1273-1281). A related method, hydrolysis, entails the solvolytic cleavage of PET as shown in FIGS. 1B and 1C (alcoholysis and aminolysis respectively), and yields monomer forms ethylene glycol and derivatives of terephthalic acid: esters and amides, respectively. Similarly to glycolysis, these reactions often require high temperatures upwards of 250° C., and pressures between 1.5 and 2 MPa.

Hydrolysis can occur in neutral, acidic, or basic conditions. Under neutral conditions, steam can be used to depolymerize PET, although the reaction is slow in the absence of added inorganic salts or organic cosolvents. The alkaline hydrolysis of PET is usually carried out in a concentrated solution of potassium hydroxide or sodium hydroxide. The four products of this reaction are ethylene glycol and the dipotassium or disodium terephthalate salt (Hu, L.-C.; Oku, A.; Yamada, E.; Tomari, K. Alkali-decomposition of poly (ethylene terephthalate) in mixed media of nonaqueous alcohol and ether. Study on recycling of poly (ethylene terephthalate). *Polym. J.* 1997, 29, 708-712; and Yoshioka, T.; Sato, T.; Okuwaki, A. Hydrolysis of waste PET by sulfuric acid at 150° C. for a chemical recycling. *J. Appl. Polym. Sci.* 1994, 52, 1353-1355). For the acidic hydrolysis of PET, concentrated sulfuric acid (>10 M), nitric acid, and phosphoric acid (Mishra, S.; Goje, A.; Zope, V. Chemical recycling, kinetics, and thermodynamics of poly (ethylene terephthalate)(PET) waste powder by nitric acid hydrolysis. *Polym. React. Eng.* 2003, 11, 79-99) are used. Acid hydrolysis and alkaline hydrolysis are inherently corrosive as high concentrations of acid or base can corrode the reaction vessels and therefore shorter reaction times and lesser corrosive chemical recycling alternatives are necessary for the long term implementation of chemical recycling methods on scale.

SUMMARY

In accordance with the purposes of the disclosed materials and methods, as embodied and broadly described herein, the disclosed subject matter, in one aspect, relates to methods of degradation of polymers. In particular, a method for electrochemical degradation of a polyester is provided, the method comprising:

A method for electrochemical degradation of a polyester comprising:
a) providing an electrochemical cell comprising a cathode, wherein the cathode is in electrical communication with a mixture comprising the polyester and an alcoholic solvent; and
b) passing a current through the cathode to form one or more degradation products of the polyester.

A system for the electrochemical degradation of polyesters is also provided, the system comprising:
a reaction vessel;
a mixture within the reaction vessel, the mixture comprising the polyester and an alcoholic solvent;
a cathode in electrical communication with the mixture; and
a power source in electrical communication with the cathode.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DESCRIPTION OF DRAWINGS

Like reference symbols in the various drawings indicate like elements.

DETAILED DESCRIPTION

The following description of the disclosure is provided as an enabling teaching of the disclosure in its best, currently known embodiments. Many modifications and other embodiments disclosed herein will come to mind to one skilled in the art to which the disclosed methods and compositions and devices used therein pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As can be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It can be further understood that terms, such as those defined in commonly used dictionaries, should be interpreted as having a meaning that is consistent with their meaning in the context of the specification and relevant art and should not be interpreted in an idealized or overly formal sense unless expressly defined herein. Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "an electrode", "a polyester", or "a solvent", includes, but is not limited to, two or more such electrodes, polyesters, or solvents, and the like.

It should be noted that ratios, concentrations, amounts, and other numerical data can be expressed herein in a range format. It can be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it can be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about"

whether or not expressly stated to be such. It is understood that where "about," "approximate," or "at or about" is used before a quantitative value, the parameter also includes the specific quantitative value itself, unless specifically stated otherwise.

As used herein, the terms "optional" or "optionally" means that the subsequently described event or circumstance can or cannot occur, and that the description includes instances where said event or circumstance occurs and instances where it does not.

Compounds are described using standard nomenclature. Unless defined otherwise, all technical and scientific terms used herein have the same meaning as is commonly understood by one of skill in the art to which this invention belongs.

The compounds described herein include enantiomers, mixtures of enantiomers, diastereomers, tautomers, racemates and other isomers, such as rotamers, as if each is specifically described, unless otherwise indicated or otherwise excluded by context. It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form. Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Methods for Electrochemical Degradation of Polyesters

The present disclosure provides methods for the degradation of polyesters, in particular the degradation of polyesters via electrochemical methods. The presently disclosed methods allow for the chemical recycling of monomeric components for the polyester polymers. Further, the presently disclosed methods occur under mild conditions (e.g., at or near ambient temperature) and avoid the use of stoichiometric quantities of strong bases Thus, in one aspect, a method is provided for electrochemical degradation of a polyester comprising:
  a) providing an electrochemical cell comprising a cathode, wherein the cathode is in electrical communication with a mixture comprising the polyester and an alcoholic solvent; and
  b) passing a current through the cathode to form one or more degradation products of the polyester.

Representative examples of alcoholic solvents which may be used in the above method include, but are not limited to, tert-amyl alcohol, benzyl alcohol, 1,4-butanediol, 1,2,4-butanetriol, butanol, 1-butanol, 2-butanol, tert-butyl alcohol, denatured alcohol, di(propylene glycol) methyl ether, diethylene glycol, ethanol, ethylene glycol, 2-ethylhexanol, furfuryl alcohol, glycerol, isobutanol, isopropyl alcohol, methanol, 2-(2-methoxyethoxy)ethanol, 2-methyl-1-butanol, 2-methyl-1-pentanol, 3-methyl-2-butanol, neopentyl alcohol, 2-pentanol, 1,3-propanediol, 1-propanol, propylene glycol, and propylene glycol methyl ether. In particular embodiments, the alcoholic solvent may comprise methanol, ethanol, isopropanol, and tert-butyl alcohol.

In some embodiments, the mixture may further comprise water. In some embodiments, the ratio of the alcoholic solvent to water may range from about 90:10 to about 10:90, for example the ratio may be about 90:10, about 80:20, about 70:30, about 60:40, about 50:50, about 40:60, about 30:70, about 20:80, or about 10:90, including any and all ranges and subranges therein.

In some embodiments, the mixture may further comprise one or more additional organic solvents, for example an ethereal solvent such as tetrahydrofuran or 1,4-dioxane.

In some embodiments, the mixture may further comprise an electrolyte. In some embodiments, the electrolyte may comprise an alkali metal halide, for example sodium chloride or potassium chloride. In some embodiments, the electrolyte may comprise an alkali metal nitrate, for example sodium nitrate. In some embodiments, the electrolyte may comprise an alkali metal triflate, for example sodium triflate. In some embodiments, the electrolyte may comprise an alkylammonium halide, for example a tetraalkylammonium halide such as tetrabutylammonium chloride. In some embodiments, the electrolyte may comprise a tetraalkylammonium bistrifluoromethanesulfonimidate, for example but not limited to tetraethylammonium bistrifluoromethanesulfonimidate. Other representative examples of electrolytes which may be used include, but are not limited to, tetrabutylammonium acetate, tetrabutylammonium benzoate, tetrabutylammonium hexafluorophosphate, tetrabutylammonium perchlorate, tetrabutylammonium tetrafluoroborate, tetrabutylammonium tetraphenylborate, tetraethylammonium benzoate, tetraethylammonium chloride, tetraethylammonium hexafluorophosphate, tetraethylammonium tetrafluoroborate, and tetrapropylammonium bromide.

In some embodiments, the electrolyte is present in a concentration ranging from about 0.01 M to about 1.0 M, for example a concentration of about 0.01 M, 0.05 M, 0.1 M, 0.2 M, 0.3 M 0.4 M, 0.5 M, 0.6 M, 0.7 M, 0.8 M, 0.9 M, or 1.0 M, including any and all ranges and subranges therein.

In some embodiments, the mixture may further comprise an ionic liquid, a diverse class of liquids substantially consisting of ions. An ionic liquid can be simple and contain a single kind of anion and a single kind of cation, or may be complex and contain a mixture of different anions and/or different cations. Some ionic liquids have a low melting point and negligible vapor pressure near or below room temperature and are often referred to as room temperature ionic liquids. Ionic liquids may be formed from various combinations of cations and anions, among which at least one kind of ion is organic. The ions are preferably monovalent. Examples of cations include, but are not limited to, 1-alkyl-3-methyl imidazolium such as 1-ethyl-3-methyl imidazolium [EMIM] and 1-butyl-3-methyl imidazolium [BMIM], 1,2,3-trimethyl imidazolium, N-alkylpyridinium such as N-butyl pyridinium [BPY], pyrrolidinium, guanidinium and alkyl guanidinium, isouronium, $P(R')_4^+$, $N(R')_4^+$, $S(R')_3^+$, tetramethylammonium, choline, cocomonium, and mixtures thereof, R preferably being, independently of each other, optionally substituted alkyl, alkenyl, aryl, or hydrogen. Examples of anions include, but are not limited to, hexafluorophosphate [HFP], tetrafluoroborate [TFB], fluorosulfonate, hexafluoroantimonate, hexafluoroarsenate, chloroaluminate, bromoaluminate, bis(trifluoromethylsulfonyl)imide, tris(trifluoromethylsulfonyl)methide, tricyanomethide, dicyanamide, nonafluorobutanesulfonate, trifluoromethane sulfonate, 2,2,2-trifluoroethanesulfonate, nitrate, sulfate, phosphate, $(R')PO_4^-$, $(R')_2PO_3^-$, $(R')_2PO_2^-$ (e.g., dialkylphosphinate), perchlorate, acetate, alkylsulfonate, bis(2-ethylhexyl)s odium sulfosuccinate, diethyleneglycol monomethylethersulfate, alkyloligoethylsulfate, pivalate, tetraalkylborate, propionate, succinate, saccharinate, glycolate, stearate, lactate, malate, tartrate, citrate, ascorbate, glutamate, benzoate, salicylate, methanesulfonate, toluenesulfonate, and mixtures thereof, wherein R' is defined as herein. The ionic liquids described are often, but are not required to be, used as an alternative to the additional solvent and/or electrolytes described herein. A representative example of an ionic liquid which may be used is n-butyl imidazolium chloride.

In some embodiments, the electrochemical cell may further comprise an anode. Anode and cathode materials are well known in the art. In some embodiments, the anode composition is chosen from materials such as carbon (e.g., graphite, reticulated vitreous carbon (RVC), etc.), platinum, nickel, nichrome, stainless steel, boron-doped diamond, and the like. However, it will be readily apparent to a person having ordinary skill in the art that numerous anode materials may be employed without departing from the scope of the present invention.

In some embodiments, the anode composition is an inert conductive material. As used herein, "inert" is defined as a material that is not significantly transformed chemically during the reaction, i.e., a material that remains significantly unchanged during the reaction. In some embodiments, an inert conductive material is >99% chemically unreacted during the reaction. In some embodiments, an inert conductive material is >95% chemical unreacted during the reaction. It will be readily apparent to a person having ordinary skill in the art that numerous inert conductive materials may serve as an anode under the reaction conditions described herein.

In some embodiments, the cathode composition is chosen from materials such as carbon (e.g., graphite, reticulated vitreous carbon (RVC), etc.), platinum, nickel, and the like. However, it will be readily apparent to a person having ordinary skill in the art that numerous other cathode materials may be employed without departing from the scope of the present invention.

The electrochemical cell may comprise a single compartment for the anode and the cathode or be divided and comprising separate anode and cathode compartments, optionally with one or several compartments in-between, for example an electrodialysis stack enabling any known electrodialysis to be performed. The means for separating the compartments may be a non-selective physical barrier, e.g., a porous membrane or diaphragm, or it may be selectively permeable for certain species such as cations or anions. Also a combination of membranes may be used, such as bipolar membranes. Non-selective barrier may, for example, be made from asbestos, ceramics, glass, polyolefins, PTFE, PVC, and the like. Cation selective membranes may, for example, be made from organic polymers such as PTFE, polystyrene, styrene/divinylbenzene or vinylpyridine/divinylbenzene modified with acidic groups like sulfonate, carboxylate, or phosphonate. Anion selective membranes may, for example, be made from organic polymers such as PTFE, polystyrene, styrene/divinylbenzene or vinylpyridine/divinylbenzene modified with basic groups such as quaternary ammonium. A bipolar membrane may comprise an anion permeable membrane and a cation permeable membrane laminated together, optionally with a catalyst layer in-between. Ion selective and bipolar membranes are commercially available, for example, under the trademarks Nation®, Flemium®, and Neosepta bipolar®.

In some embodiments, the electrochemical cell may comprise a cylindrical batch reactor having an inner cylinder house within an outer cylinder. In some embodiments, the inner cylinder comprise the anode and the outer cylinder comprises the cathode. In other embodiments, the inner cylinder comprises the cathode and the outer cylinder comprises the anode. In other embodiments, the electrochemical cell comprises a divided flow cell, for example a parallel plate reactor, a bipolar rotating disk reactor, or a fluidized bed reactor.

Further representative examples of electrochemical cells which may be used in the methods of the present disclosure include, but are not limited to, those described in Lin, R. et al. "Electrochemical Reactors for $CO_2$ Conversion" Catalysts 2020, 10, 473.

In some embodiments, a current is passed through the anode that generates a cathodic potential ranging from about −2.5 volts (V) to about −1.7 volts (V) versus the silver/silver (I) chloride redox couple in a three-electrode configuration. In some embodiments, the cathodic potential may be, for example, −2.5 V, −2.4 V, −2.3 V, −2.2 V, −2.1 V, −2.0 V, −1.9 V, −1.8 V, or −1.7 V, including any and all ranges and subranges therein.

In some alternative embodiments, the method may further comprise:
  c) heating the mixture to a temperature ranging from about 40 degrees Celsius to about 80 degrees Celsius following b).

In some embodiments, the mixture may be heated to a temperature ranging from about 40° C. to about 70° C., from about 40° C. to about 60° C., from about 40° C. to about 50° C., from about 50° C. to about 80° C., from about 50° C. to about 70° C., from about 50° C. to about 60° C., from about 60° C. to about 80° C., from about 60° C. to about 70° C., or from about 70° C. to about 80° C. In some embodiments, the mixture may be heated to a temperature of about 40° C., about 45° C., about 50° C., about 55° C., about 60° C., about 65° C., about 70° C., about 75° C., or about 80° C.

In some alternative embodiments, steps b) and c) may be repeated for about one or more cycles. In some embodiments, steps b) and c) are repeated for one, two, three, four, five, six, seven, eight, nine, ten, or more cycles.

In order to avoid detrimental accumulation of impurities from feed chemicals or from side reactions it may in some cases be advisable to bleed off part of the mixture from the cell and/or purify with various methods such as electrodialysis, adsorption, recrystallization, precipitation, washing, ion-exchange, evaporation or stripping using a carrier gas, or reactive regeneration with acid/base or reductive/oxidative steps.

Methods for Batch Chemical Degradation of Polyesters

In another aspect, a method is provided for the chemical degradation of a polyester, the method comprising heating the polyester in the presence of mixture comprising a hydroxide base and an alcoholic solvent at a temperature ranging from about 40° C. to about 100° C.

In some embodiments, the hydroxide base may be selected from the group consisting of sodium hydroxide, potassium hydroxide, lithium hydroxide, cesium hydroxide, calcium hydroxide, or magnesium hydroxide.

Representative examples of alcoholic solvents which may be used in the above method include, but are not limited to, tert-amyl alcohol, benzyl alcohol, 1,4-butanediol, 1,2,4-butanetriol, butanol, 1-butanol, 2-butanol, tert-butyl alcohol, denatured alcohol, di(propylene glycol) methyl ether, diethylene glycol, ethanol, ethylene glycol, 2-ethylhexanol, furfuryl alcohol, glycerol, isobutanol, isopropyl alcohol, methanol, 2-(2-methoxyethoxy)ethanol, 2-methyl-1-butanol, 2-methyl-1-pentanol, 3-methyl-2-butanol, neopentyl alcohol, 2-pentanol, 1,3-propanediol, 1-propanol, propylene glycol, and propylene glycol methyl ether. In particular embodiments, the alcoholic solvent may comprise methanol, ethanol, isopropanol, and tert-butyl alcohol.

In some embodiments, the mixture may further comprise water. In some embodiments, the ratio of the alcoholic solvent to water may range from about 90:10 to about 10:90, for example the ratio may be about 90:10, about 80:20, about 70:30, about 60:40, about 50:50, about 40:60, about 30:70, about 20:80, or about 10:90, including any and all ranges and subranges therein.

In some embodiments, the mixture may further comprise one or more additional organic solvents, for example an ethereal solvent such as tetrahydrofuran or 1,4-dioxane.

In some embodiments, the mixture may be heated to a temperature of about 40° C., about 45° C., about 50° C., about 55° C., about 60° C., about 65° C., about 70° C., about 75° C., about 80° C., about 85° C., about 90° C., about 95° C., or about 100° C.

In some embodiments, the mixture may be heated by the use of microwave irradiation. Microwaves act as high frequency electric fields and will generally heat any material containing mobile electric charges, such as polar molecules in solvent. Polar solvents are heated as their component molecules are forced to rotate with the field and lose energy in collisions. Acting as an internal heat source, microwave absorption is able to heat the target compounds without heating the entire furnace or oil bath, which saves time and energy. Numerous microwave reactors in which the above method can be performed are commercially available and would be familiar to a person of ordinary skill in the art.

Polyesters

The methods described in the present disclosure are useful for the degradation of polyesters to simpler chemical components that may be subsequently recycled. A polyester is defined as a synthetic linear polymer whose repeating contains contain ester functional groups, wherein these ester functional groups are integral members of the linear polymer chain.

Typical polyesters as may be used in the present disclosure were formed by condensation of a dicarboxylic acid and a diol. Representative examples of such dicarboxylic acids include terephthalic acid, isophthalic acid, 2,6-napthalene dicarboxylic acid, 3,4'-diphenylether dicarboxylic acid, hexahydrophthalic acid, 2,7-naphthalenedicarboxylic acid, phthalic acid, 4,4'-methylenebis(benzoic acid), oxalic acid, malonic acid, succinic acid, methyl succinic acid, glutaric acid, adipic acid, 3-methyladipic acid, pimelic acid, suberic acid, azelaic acid, sebacic acid, 1,11-undecanedicarboxylic acid, 1,10-dodecanedicarboxylic acid, undecanedioic acid, 1,12-dodecanedicarboxylic acid, hexadecanedioic acid, docosanedioic acid, tetracosanedioic acid, 1,4-cyclohexanedicarboxylic acid, 1,3-cyclohexanedicarboxylic acid, 1,2-cyclohexanediacetic acid, fumaric acid, and maleic acid. Representative examples of such diols include monoethylene glycol, diethylene glycol, triethylene glycol, poly(ethylene ether)glycols, 1,3-propanediol, 1,4-butanediol, poly(butylene ether)glycols, pentamethylene glycol, 1,6-hexanediol, 1,8-octanediol, 1,10-decanediol, 1,12-dodecanediol, 1,14-tetradecanediol, 1,16-hexadecanediol, cis-1,4-cyclohexanedimethanol, and trans-1,4-cyclohexanedimethanol. Accordingly, the above dicarboxylic acids and/or diols may comprise at least a portion of the one or more degradation products of a polyester formed previously by condensation of the dicarboxylic acids and/or diols.

Representative examples of such polyesters as may be used in the present disclosure include poly(ethylene terephthalate) (PET), poly(trimethylene terephthalate) (PTT), poly(butylene terephthalate) (PBT), poly(ethylene isophthalate), poly(octamethylene terephthalate), poly(decamethylene terephthalate), poly(pentamethylene isophthalate), poly(butylene isophthalate), poly(hexamethylene isophthalate), poly(hexamethylene adipate), poly(pentamethylene adipate), poly(pentamethylene sebacate), poly(hexamethylene sebacate), poly(1,4-cyclohexylene terephthalate), poly(1,4-cyclohexylene sebacate), poly(ethylene terephthalate-co-sebacate), and poly(ethylene-co-tetramethylene terephalate).

In other embodiments, the polyester as used in the present disclosure were formed by condensation of a hydroxy-substituted carboxylic acid or ester or derivative thereof, for example a lactone. Representative examples of such polyesters include, but are not limited to, polyglycolic acid (PGA), polylactic acid (PLA), polycaprolactone (PCL), polyhydroxyalkanoates (PHAs), and polyhydroxybutyrate (PHB). Representative degradation products include glycolic acid (for PGA), lactic acid (for PLA), caproic acid (for PCL), hydroxyalkanoic acids (for PHAs), and hydroxybutyric acid (for PHB).

In particular embodiments, the polyester comprises polyethylene terephthalate (PET). In such embodiments, the one or more degradation products comprise ethylene glycol and terephthalic acid.

In particular embodiments, the polyester comprises polybutylene terephthalate (PBT). In such embodiments, the one or more degradation products comprise butylene glycol and terephthalic acid.

In particular embodiments, the polyester comprises polyethylene napthalate (PEN). In such embodiments, the one or more degradation products comprise ethylene glycol and naphthalene-2,6-dicarboxylic acid.

In particular embodiments, the polyester comprises polylactic acid. In such embodiments, the one or more degradation products comprise lactic acid.

A number of embodiments of the disclosure have been described. Nevertheless, it will be understood that various modifications may be made without departing from the spirit and scope of the invention. Accordingly, other embodiments are within the scope of the following claims.

By way of non-limiting illustration, examples of certain embodiments of the present disclosure are given below.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variants of the present invention, which are apparent to one skilled in the art.

Efforts have been made to ensure accuracy with respect to numbers (e.g., amounts, temperature, etc.), but some errors and deviations should be accounted for. Unless indicated otherwise, parts are parts by weight, temperature in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1. Chemical and Electrochemical Recycling of End-Use Poly(ethylene terephthalate) (PET) Plastics in Batch, Microwave and Electrochemical Reactors Given the known recycling methods, the ubiquity of PET plastics, and the knowledge gaps identified in the field, this example aims to provide additional chemical recycling alternatives for the recovery of monomeric materials from end-use PET. We first focused on the optimization of the basic hydrolysis of this end-use polymer. In purely aqueous conditions, we observed yields of terephthalic acid of up to 23% after 48 h at reflux (Entry 3, Table 1). Similar yields are obtained after only 4 h upon switching the solvent to methanol (Entry 1, Table 1). A 12 h reaction time produced 75% of the expected terephthalic acid (Entry 2, Table 1). We note that the maximum % yield of recovered terephthalic acid from end-use PET is affected by the presence of plasticizers and additives, including siloxanes which were detected using GC-EI. Tomari and coworkers report complete decomposition of PET plastic under similar conditions to occur in 7 h, with acceleration to 40 min of reaction time observed by adding a 10% volume of 1,4-dioxane. While their report is an important advance, ethereal solvents are peroxide formers (Clark, D. E. Peroxides and peroxide-forming compounds. *Chem. Health Saf.* 2001, 8, 12-22) and pose a significant hazard when used industrially on large scale. They are most often stabilized by radical-inhibitors such as BHT. The presence of radical inhibitors introduces the need for additional separation steps and consequently raises costs (Fujisawa, S.; Kadoma, Y.; Yokoe, I. Radical-scavenging activity of butylated hydroxytoluene (BHT) and its metabolites. *Chem. Phys. Lip.* 2004, 130, 189-195).

TABLE 1

Screening conditions for depolymerization of PET plastic.

| Reaction Entry | Conditions[a] | Reaction Time | Terephthalic Acid Yield % [b] |
|---|---|---|---|
| 1 | MeOH, reflux | 4 h | 23 |
| 2 | MeOH, reflux | 12 h | 75 |
| 3 | Water, reflux | 48 h | 23 |

[a]Reactions were run at reflux with 100 mg commercial PET plastic from a standard water bottle.
[b] Yield based on terephthalic acid after acidic workup.

Given the limitation of ethereal accelerants and advances in synthetic methodologies based on microwave reactors (Kappe, C. O.; Dallinger, D. The impact of microwave synthesis on drug discovery. *Nat. Rev. Drug Discov.* 2006, 5, 51-63), combined with reports related to the recycling of PET plastics through microwave digestion in aqueous conditions with the use of phase-transfer catalysts (Siddiqui, M. N.; Achilias, D. S.; Redhwi, H. H.; Bikiaris, D. N.; Katsogiannis, K. A. G.; Karayannidis, G. P. Hydrolytic depolymerization of PET in a microwave reactor. *Macromol. Mater. Eng.* 2010, 295, 575-584), we proceeded to investigate the depolymerization of end-use PET in conditions similar to Table 1, Entry 2. In the microwave, temperatures above the solvent boiling points can be achieved, thus producing higher reaction rates and lowered reaction times. The results of our studies are summarized in Table 2.

TABLE 2

Microwave reactions for the depolymerization of poly(ethylene terephthalate).

| Reaction Entry | Conditions [a] | Reaction Time | Terephthalic Acid Yield % |
|---|---|---|---|
| 1 | Water, 170° C. | 30 min | 0 |
| 2 | MeOH, 85° C. | 13 min | 55 |
| 3 | MeOH, 85° C. | 40 min | 65 |
| 4 | MeOH, 130° C. | 40 min | 65 |

[a] Reactions were run in 20 mL CEM GlassChem vessels equipped with magnetic stir bars charged with 14 mL solvent and 10 mg end-use PET and 3.75M NaOH with a maximum power of 1000 W.

In these experiments, under exclusively aqueous conditions, we did not observe any PET breakdown, even at a temperature of 170° C. (Table 2 Entry 1). Gratifyingly, in 13 min at 85° C. in methanol, we observed 55% terephthalic acid yield which increased to 65% with a longer reaction time of 40 min (Table 2 Entry 3). An increase in temperature to 130° C. did not produce a higher yield. We believe this is due to a combination of factors related to mass transport and stirring limitations in the reactor.

TABLE 3

Reactions at room temperature (21° C.), for 1 h in a batch electrolysis H-Cell divided by a coarse ceramic frit at controlled potential against a single-junction Ag/AgCl reference electrode with 20 mg PET plastic.

| Reaction Entry | Conditions | Terephthalic Acid Yield %[a] | $nCO_2 * 10^{-6}$[b] |
|---|---|---|---|
| 1 | 50% MeOH in water, −2.2 V | 16.9 | 7.89 ± 0.36 |
| 2 | Water, 0.1M NaCl, −2.2 V | 0.51 | n/a[c] |

[a]Yield of terephthalic acid obtained after the acidic workup of the cell contents.
[b]Amount of $CO_2$ produced in the anode was calculated from the quantitation of a $CO_2$ sample from the anode headspace by GC-TCD (thermal conductivity detection) on a PLOT 1010 column quantified against standards.
[c]$CO_2$ signal present, but below quantitation limit.

Given our experience in the field of electrolytic hydrogen production (Luca, O. R.; Blakemore, J. D.; Konezny, S. J.; Praetorius, J. M.; Schmeier, T. J.; Hunsinger, G. B.; Batista, V. S.; Brudvig, G. W.; Hazari, N.; Crabtree, R. H. Organometallic Ni pincer complexes for the electrocatalytic production of hydrogen. *Inorg. Chem.* 2012, 51, 8704-8709; Luca, O. R.; Konezny, S. J.; Blakemore, J. D.; Colosi, D. M.; Saha, S.; Brudvig, G. W.; Batista, V. S.; Crabtree, R. H. A tridentate Ni pincer for aqueous electrocatalytic hydrogen production. *New J. Chem.* 2012, 36, 1149-1152; and Mast, Z. J.; Myren, T. H.; Huntzinger, C. G.; Stinson, T. A.; Kharbouch, R. M.; Almanza, E. M.; Zygmont, S. E.; Miecznikowski, J. R.; Luca, O. R. Cu I SNS triazole and imidazole pincers as electrocatalyst precursors for the production of solar fuels. *Inorg. Chem. Front.* 2020, 7, 1012-1015) and reductive electrocatalysis (Myren, T. H.; Lilio, A. M.; Huntzinger, C. G.; Horstman, J. W.; Stinson, T. A.; Donadt, T. B.; Moore, C.; Lama, B.; Funke, H. H.; Luca, O. R. Manganese N-heterocyclic carbene pincers for the electrocatalytic reduction of carbon dioxide. *Organometallics* 2018, 38, 1248-1253; and Myren, T. H.; Alherz, A.; Thurston, J. R.; Stinson, T. A.; Huntzinger, C. G.; Musgrave, C. B.; Luca, O. R. Mn-Based Molecular Catalysts for the Electrocatalytic Disproportionation of $CO_2$ into CO and $CO_3^{2-}$. *ACS Catal.* 2020, 10, 1961-1968), we investigated the electrochemical generation of the necessary basic conditions using current passage through a protic medium (Scheme 1). We hypothesized that this methodology would have a distinct advantage over the batch and microwave methods occurring at room temperature in neutral salted media, with the necessary base generated in situ (Scheme 1) at rates that one can control by dialing in the delivery of charge in coulombs/s. This electrochemical method avoids the use of corrosive solutions that may pose a significant limitation in the scaling of the chemical recycling process. The results of our studies are shown in Table 3.

Scheme 1. Electrochemical generation of base from protic media for the electrochemical depolymerization of PET plastic at neutral starting conditions.

Electrolysis in aqueous conditions at −2.2V vs. Ag/AgCl, (Table 3 Entry 3) resulted in low levels of breakdown of the PET plastic. This observation agrees with our prior results in the batch and microwave reactions. When the solvent is changed to 1:1 methanol/water, however, a one-hour electrolysis was able to produce a yield of 17% of terephthalic acid (Table 3 Entry 1). In addition, we also observe the formation of carbon dioxide in the headspace of our anode chamber, which likely correlates to the migration of the TPA across the frit of our electrochemical reactor and subsequent Kolbe decarboxylation (Conway, B.; Dzieciuch, M. New Approaches to the Study of Electrochemical Decarboxylation and the Kolbe Reaction: Part I. The Model Reaction with Formate. *Can. J. Chem.* 1963, 41, 21-37; and Conway, B.; Dzieciuch, M. New Approaches to the Study of Electrochemical Decarboxylation and the Kolbe Reaction: Part II. The Model Reaction with Trifluoroacetate and Comparisons with Aqueous Solution Behavior. *Can. J. Chem.* 1963, 41, 38-54). This establishes a proof of concept for an electrochemical method for hybrid chemical and quaternary recycling, as an alternative to combustive methods.

Conclusion

In conclusion, we now report that the decomposition of PET plastic and recovery of terephthalic acid can be achieved with relatively mild conditions in alkaline methanol both in batch and in the microwave. Microwave reactions occurred with reaction times as short as 40 min at only 85° C. In addition, we report that base generated in an electrochemical reaction in the presence of end use PET can cause the breakdown of the polymer at room temperature without the use of highly corrosive media. While the yields of the electrochemical reaction remain modest, they provide an important advance in the arena of sustainable chemical recycling on scale.

Materials and Methods

General Methods

Materials, reagents, and solvents were obtained from commercial sources without further purification unless otherwise noted. $^1$H-NMR spectra for the characterization and yield analysis of depolymerization products were taken on a Bruker AV-III 300 MHz NMR Spectrometer (Billerica, MA, USA)) at room temperature in DMSO-$d_6$. Poly(ethylene terephthalate) (PET) was obtained from Sam's Choice Purified Drinking Water bottles which were emptied, cleaned, and then sheered with scissors into smaller pieces.

PET Depolymerization in Batch and Microwave

PET was depolymerized in a 3.75 M solution of sodium hydroxide in methanol unless otherwise noted. The reaction solution was then placed in a round bottom flask and was dried on a rotary evaporator followed by high-vacuum to remove residual methanol. The resulting white solids consisted of sodium hydroxide and disodium terephthalate which were then re-dissolved in a minimal amount of water. For experiments run in water instead of methanol, this step was omitted. The flask was placed in a water ice bath with stirring. The solution was acidified with hydrochloric acid, and verified with pH paper, to obtain terephthalic acid (TPA). The flask was again placed on the rotary evaporator with a hot water bath followed by high-vacuum to dry. Ethyl acetate was added to the flask, heated to 60° C. (Sheehan, R. J. Terephthalic Acid, Dimethyl Terephthalate, and Isophthalic Acid. In *Ullmann's Encyclopedia of Industrial Chemistry*, John Wiley & Sons: Hoboken, NJ, 2011), then sonicated to dissolve the TPA and separate the depolymerization product from the sodium chloride salt. The TPA/ethyl acetate solution was filtered into another round bottom flask. This process was repeated twice. After drying, a white film was observed on the inside of the round bottom flask (FIG. 2).

DMSO-$d_6$ was used as the NMR solvent to dissolve the entire TPA sample and a $^1$H-NMR was taken to confirm the presence of TPA as a depolymerization product. Bibenzyl was added as an internal standard and yield was calculated by NMR as follows:

Calculated the ratio of TPA (T) to bibenzyl (B):

$$\frac{\frac{integral_T}{integral_B}}{\frac{protons_T}{protons_B}} = ratio_{T/B} \qquad (1)$$

Calculated the moles of bibenzyl:

$$\frac{m_B}{MW_B} = \mathrm{mol}_B \quad (2)$$

Calculated the moles of TPA:

$$\mathrm{mol}_B \times \mathrm{ratio}_{T/B} = \mathrm{mol}_T \quad (3)$$

Calculated the mass of TPA:

$$\mathrm{mol}_T \times MW_T = m_{Texp} \quad (4)$$

Calculated the theoretical mass of TPA:

$$m_{PET} \times \frac{1}{PW_{PET}} \times MW_T = m_{Ttheo} \quad (5)$$

Calculated the experimental yield by NMR:

$$\frac{m_{Texp}}{m_{Ttheo}} \times 100 = \% \text{ yield of } T \quad (6)$$

where m is mass, MW is molecular weight, FW is the formula weight.

The expected yield of terephthalic acid was calculated based on a theoretical 100% monomer consisting of one terephthalic acid and one ethylene glycol fragment. The reported yields are therefore likely an underestimation of the yield due to the prevalence of unknown additives and plasticizers (Guart, A.; Bono-Blay, F.; Borrell, A.; Lacorte, S. Migration of plasticizersphthalates, bisphenol A and alkylphenols from plastic containers and evaluation of risk. *Food Addit. Contam. A* 2011, 28, 676-685). When analyzed by GC-EI, evidence of potential plasticizers was found.

Microwave Experiments

Reactions were run in a 2450 MHz CEM Mars 6 Microwave (Matthews, NC, USA) equipped with a fiber optic temperature probe. 20 mL CEM GlassChem vessels equipped with magnetic stir bars were charged with a maximum of 14 mL of solvent per vessel and a minimum total solvent volume of 50 mL. Vessels were capped using standard GlassChem covers and a control vessel was equipped with a sapphire thermowell for temperature monitoring. All vessels were sealed to allow for pressure buildup. The reactions were ramped to temperature, maintaining a ramp rate from 11-13° C. and never exceeding 1000 W of power.

Electrochemistry Experiments and Gas Chromatography

Controlled potential electrolyses for headspace analysis were performed in a custom H-cell equipped with the anode and cathode chambers separated by a glass frit with a separated headspace. The working electrode chamber contained a glassy carbon plate electrode and a BASi single junction Ag/AgCl (3 M NaCl) reference electrode. The counter electrode chamber contained a high-surface-area carbon cloth. Before electrolysis, the solution was sparged with argon and the cell was evacuated and backfilled with argon three times. Electrolyses were run with 20 mL in each chamber of a 50% MeOH in HPLC water solution with 0.1 M NaCl as supporting electrolyte.

Gas chromatographic analysis was performed on a Hewlett Packard 5890 Series II gas chromatograph equipped with a thermal conductivity detector (TCD) and flame ionization detector (FID) in series with a Carboxen-1010 PLOT capillary column (Bellefonte, PA, USA). Argon was used as the carrier gas. The flow rate was 3 mL/min. Flow and make up was 6 mL/min. The reference gas flow was 19 mL/min. The FID has no auxiliary gas, air flow was at 350 mL/min and H2 was at 35 mL/min. The inlet was heated to 200° C. and the oven started at a temperature of 35° C. which was held for 8 min before a ramp of 20° C./min up to 195° C. which was held for 1 min. A gas-tight analytical syringe (Hamilton 1750, 500 µL,) was used to collect 200 µL aliquots for analysis.

Identification of Plasticizers by GC-EI

Data were collected on a Thermo ISQ LT GC-MS in EI mode with an electron energy of 70 eV (Waltham, MA, USA). The column used was a Zebron ZB-5HT (30 m×0.25 mm inside diameter, 0.25 µm film thickness, Newport Beach, CA, USA). Samples were collected in split mode with a column flow of 1 mL/min, purge flow of 10 mL/min, and a split flow of 10 mL/min Inlet and ion source temperatures were held at 200° C. and 180° C. respectively. Samples for injection were prepared by diluting one drop of depolymerization NMR sample in 1 mL of methanol and an aliquot (1 µL) of the dilution was injected. The oven starting temperature was 70° C. held for 1 min followed by a ramp of 60° C./min up to 300° C. which was held for 6 min. Data were collected using Chromeleon software. Mass spectra from peaks in the total ion chromatograph were compared to a NIST database using the software which listed possible matches with % probability. The results are summarized in Table 4.

TABLE 4

| Potential plasticizers identified using GC-EI. | |
|---|---|
| Compound | Prob (%) |
| Dodecamethylcyclohexasiloxane | 86.89 |
| Tetradecamethylcyclohexasiloxane | 86.89 |
| Hexadecamethylcyclooctasiloxane | 75.73 |
| Octasiloxane | 66.82 |

Example 2. Chemical and Electrochemical Recycling of Other Polyester Plastics in Batch, Microwave and Electrochemical Reactors Polylactic Acid Polylactic Acid (PLA)    Lactic acid

TABLE 5

| Reaction Number | Concentration | Method | % mass recovered of lactic acid |
|---|---|---|---|
| 1 | 7.70 mM | Reflux, 18 h | 52.11% |
| 2 | 7.73 mM | Microwave, 130° C., 40 min | 22.23% |
| 3 | 5.60 mM | Electrolysis, −2.2 V vs. Ag/AgCl, 1 h | 5.39% |

Depolymerization reactions performed on the substrate polylactic acid (PLA). Reflux and microwave reactions used 3.75M NaOH in methanol while the electrolysis was done in a 0.1M NaCl solution of 50% water/50% methanol. The microwave reaction additionally had a ramp rate of 13° C./min and a power of 1000 W.

In Table 5, reaction 1, a solution of 3.75 M NaOH in 200 mL of methanol was added to a round bottom with a reflux condenser. 111.01 mg (7.70 mM) of polylactic acid (PLA) was added along with a stir bar and the entire reaction was refluxed for 18 hours. The reaction was removed from heat and the solvent was removed via rotary evaporator. The resulting solid was redissolved with HPLC water and acidified with HCl. After drying by rotary evaporator again, a 0.02639 g aliquot of the 43.79 g sample was dissolved in DMSO-$d_6$ with 0.01143 g of bibenzyl as internal standard. Calculations from the NMR found 52.11% mass lactic acid recovered.

Table 5, reaction 2 and 3 show two trials of the microwave based depolymerization method for PLA. In each, a 3.75 M NaOH in methanol solution was prepared and added to the microwave vessel with a stir bar. To this, 7.73 mM and 8.43 mM PLA was added, respectively. The microwave was programmed with a ramp rate of 13° C./min, a reaction time of 40 min, reaction temperature of 130° C., and a power of 1000 watts. After the reaction was complete, solvent was removed under vacuum and solid was dried before redissolving in water and acidifying. After solvent removal and another drying step, ethyl acetate was used for extraction and dried. An aliquot of the resulting solid was dissolved in DMSO-$d_6$. From the NMR, a 22.23% mass recovered of lactic acid was determined.

Table 5, reaction 4 shows the electrolysis depolymerization of PLA. The electrolysis solution is 20 mL of a 0.1 M NaCl solution in 50% water/50% MeOH. 8.07 mg (2.62 mM) of PLA was added to the working chamber. A potential of −2.2 V vs. Ag/AgCl was applied for 1 hour. Solutions from the anode and cathode were worked up in parallel starting with stripping the solvent followed by redissolving in water and acidifying before a final drying step. The final solid products were dissolved in DMSO-$d_6$ with bibenzyl standard for quantification by NMR. The total % mass recovered was calculated at 5.39%.
While the electrolysis reaction did not achieve the same % mass recovery as the reflux method or one of the microwave trials, it was comparable to the second microwave trial and did achieve breakdown of the polymer in 1 hour without any added base.

Polybutylene Terephthalate (PBT)

Polybutylene Terephthalate (PBT)

Terephthalic Acid + Butanediol

TABLE 6

| Reaction Number | Concentration | Method | % mass recovered of TPA |
|---|---|---|---|
| 4 | 2.62 mM | Reflux, 12 h | 18.23% |
| 5 | 12.37 mM | Microwave, 130° C., 40 min | 15.43% |
| 6 | 2.61 mM | Electrolysis, −2.2 V vs. Ag/AgCl, 1 h | Tbd |
| 7 | 2.55 mM | Electrolysis, −2.2 V vs. Ag/AgCl, 1 h | Tbd |

Depolymerization reactions performed on the substrate polybutylene terephthalate (PBT). Reflux and microwave reactions used 3.75M NaOH in methanol. Electrolysis used 0.1M NaCl solution of 50% water/50% methanol. The microwave reaction had a ramp rate of 13° C./min and a power of 1000 W.

The reflux reaction of polybutylene terephthalate (PBT) (Table 6, reaction 4) was setup with 200 mL of 3.75 M NaOH in methanol solution and 115.36 mg of PBT (2.62 mM) with stirring at reflux for 12 hours. After cooling to room temperature, the solvent was removed with rotary evaporation. The solids were redissolved in HPLC water, acidified, and solvent was removed again. A final hot ethyl acetate extraction step was performed before a final drying to obtain a white solid. This solid was dissolved in DMSO-$d_6$ with an added bibenzyl standard. The resulting % mass recovered of terephthalic acid (TPA) was 18.23%. The microwave reaction was also run in 3.75 M NaOH in methanol but with 12.37 mM PBT added. After a 40 min reaction time at 130° C., the reaction was worked up analogously to the reflux reaction. The mass recovered was 15.43% (Table 6, reaction 5).

Two electrolysis reactions (Table 6, reactions 6 and 7) were attempted. Each was run used 50% water/50% methanol and 0.1 M NaCl added. After an hour at −2.2 V vs. Ag/AgCl the anode and cathode chamber were combined and then worked up with the same procedure as the reflux and microwave methods. However, neither of the electrolysis method samples could be quantified as one would not shim and the other resulted in a broadened NMR.

Polyethylene Napthalenate (PEN)

Polyethylene Naphthalate (PEN)

Napthalenedicarboxylic Acid + Ethylene Glycol

TABLE 7

| Reaction Number | Concentration | Method | % mass recovered of naphthalenedicarboxylic acid |
|---|---|---|---|
| 8 | 2.62 mM | Reflux, 12 h | 4.89% |
| 9 | 8.35 mM | Microwave, 130° C., 40 min | 0% |
| 10 | 2.62 mM | Electrolysis, −2.2 V vs. Ag/AgCl, 1 h | 2.2% |

Depolymerization reactions of polyethylene naphthalate (PEN). Electrolysis was prepared using a 0.1M NaCl solution of 50% water/50% methanol; reflux and microwave reactions used 3.75M NaOH in methanol. The microwave reaction had a ramp rate of 12° C./min and a power of 1000 W.

A 2.62 mM solution of polyethylene naphthalate (PEN) suspended in 200 mL of 3.75 M NaOH in methanol was prepared for the reflux reaction (Table 7, reaction 8). The reaction was run at reflux under constant stirring for 12 hours before workup. After stripping the solvent, the reaction was redissolved in water, acidified, stripped again, and extracted with hot ethyl acetate. The final solid after another stripping step was analyzed by NMR with bibenzyl standard. 4.89% mass recovered of naphthalene dicarboxylic acid was observed.

The microwave reaction (Table 7, reaction 9) was prepared analogously and run in the microwave with an increased concentration of 8.35 mM PEN, a temperature of 130° C., and a reaction time of 40 min. After the same workup method as the reflux reaction, no product was detected via NMR.

The electrolysis reaction (Table 7, reaction 10) used 40 mL of a 50% water/50% methanol mixture with added 0.1 M NaCl as the electrolyte. 2.62 mM of PEN was added and a potential of −2.2 V vs. Ag/AgCl was applied for 1 hour. After the reaction, the two chambers' solutions were combined and worked up as in the reflux and microwave experiments. Calculations from the product NMRs showed a 2.2% mass recovered of naphthalene dicarboxylic acid.

While the microwave method failed to breakdown the PEN polymer, both the reflux and electrolysis methods were successful in achieving some amount of product. The electrolysis was comparable to the reflux method with a much shorter time scale and no added base.

Example 3. Chemical and Electrochemical Depolymerization of Ester Plastics

This example describes the electrochemical and chemical depolymerization of ester thermoplastics: poly(ethyleneterephtalate) PET, poly(butyleneterephtalate) PBT, and poly(ethylenenapthalate) PEN. Under chemical basic hydrolysis conditions, we observe up to 93% mass recovered for pure PET, 44% mass recovered for PBT, and up to 41% recovery of 1,6-naphthalene dicarboxylic acid from poly(ethylenenapthalate) PEN. The latter two polymers are currently non-recyclable. Additionally, we demonstrate up to 74% mass recovery of terephthalic acid from PET using electrical current in water/methanol at carbon electrodes, conditions which are atom economical and avoid the use of highly corrosive concentrated NaOH. 32% recovery of 2,6-naphthalene dicarboxylic acid and 51% recovery of terephthalic acid are observed in the electrochemical depolymerization of a mixture of the three polymers. We use Diffusion Order Spectroscopy (DOSY) NMR to investigate the presence of oligomers in the liquid phase and surprisingly, none are observed, thus suggesting a molecular etching mechanism.

Introduction

One of the most common types of waste generated in the world is plastic waste (H. A. Petersen, T. H. Myren, S. J. O'Sullivan and O. R. Luca, Materials Advances, 2021, 2, 1113-1138). In 2018, in the United States there were 35.7 million tons of plastic generated—12.2% of municipal solid waste generation (Advancing Sustainable Materials Management: Facts and Figures Report, US EPA 2020). Plastic packaging and containers alone accounted for over 14.5 million tons of that generation. However, only about 3.1 million tons were recycled and 5.6 million tons combusted for energy recovery. The vast majority is disposed of in landfills. While mechanical methods for plastics recycling prevail, the chemical breakdown of these types of wastes is considered the only sustainable recycling method. The reason behind the low rates of plastic recycling is complex but includes the stability of the plastic polymers, quality degradation when recycling (downcycling), and chemical diversity of mixed polymer waste streams (N. Singh, D. Hui, R. Singh, I. P. S. Ahuja, L. Feo and F. Fraternali, Composites Part B: Engineering, 2017, 115, 409-422). As a consequence, energy-efficient and sustainable chemical methods for the breakdown or conversion of polymeric materials to monomers or valuable chemicals are sought (P. F. Britt, G. W. Coates, K. I. Winey, J. Byers, E. Chen, B. Coughlin, C. Ellison, J. Garcia, A. Goldman and J. Guzman, Report of the Basic Energy Sciences Roundtable on Chemical Upcycling of Polymers, USDOE Office of Science (SC)(United States), 2019). This issue is of importance for polymers relevant to food packaging such as many ester-based materials (T. H. T. Myren, T. A. Stinson, Z. J. Mast, C. G. Huntzinger and O. R. Luca, Molecules, 2020, 25, 2742).

The three ester-based thermoplastics discussed herein include poly(ethyleneterephtalate) PET, poly(butyleneterephthalate) PBT, and poly(ethylenenaphthalate) PEN. Despite the wide use of these polymers, chemical recycling methods for these feedstocks are currently limited. Methods often require harsh conditions such as high temperatures and pressures (K. Bei, P. Ma, J. Wang, K. Li, J. Lyu, Z. Hu, I.-M. Chou and Z. Pan, Polymer Engineering & Science, 2017, 57, 1382-1388; S. M. Al-Salem, P. Lettieri and J. Baeyens, Waste Management, 2009, 29, 2625-2643; R. Arai, K. Zenda, K. Hatakeyama, K. Yui and T. Funazukuri, Chemical Engineering Science, 2010, 65, 36-41; M. Yamaye, Y. Nago, M. Sasaki, T. Tsuru, K. Mukae, T. Yoshinaga, R. Murayama and C. Tahara, Polymer Degradation and Stability, 2006, 91, 2014-2021; P. Hodge, Z. Yang, A. Ben-Haida and C. S. McGrail, Journal of Materials Chemistry, 2000, 10, 1533-1537; B. Kuczenski and R. Geyer, Resources, Conservation and Recycling, 2010, 54, 1161-1169; K. Marsh and B. Bugusu, Journal of food science, 2007, 72, R39-R55; and C. Jehanno, M. M. Pérez-Madrigal, J. Demarteau, H. Sardon and A. P. Dove, Polymer Chemistry, 2019, 10, 172-186), although some copolymers are known to be biodegradable (H. Jia, M. Zhang, Y. Weng, Y. Zhao, C. Li and A. Kanwal, Journal of Environmental Sciences, 2021, 103, 50-58). PET, a semicrystalline polymer made up of terephthalic acid (TPA) and ethylene glycol monomer units, is among the most widely produced polymers. Due to its high mechanical strength and gas barrier properties, it is used in a variety of applications including fibers, films, and food packaging such as the ubiquitous plastic water bottle.

PBT is another semicrystalline polymer that is structurally similar to PET but is synthesized from terephthalic acid or dimethyl terephthalate and 1,4-butanediol to yield butyl linkers rather than ethyl (Y. Yamamoto, H. Hoshina and H. Sato, Macromolecules, 2021, 54, 1052-1062). Features such as improved solvent resistance and high processability have made this polymer a common choice for a variety of applications including automotive, electronics or substitutions for metallic materials (Z. Shen, F. Luo, H. Bai, P. Si, X. Lei, S. Ding and L. Ji, *RSC Advances*, 2016, 6, 17510-17518). PBT is not currently recycled.

PEN is a more expensive but more thermally stable, UV-resistant, and chemically resistant analogue of PET based upon 2,6-naphthalene dicarboxylic acid (NDA) rather than terephthalic acid. It is used as films, fibers, and foams in applications such as textiles and electronics (J. Yin, F. Luo, Q. Xing and M. Wang, *Polymer-Plastics Technology and Materials*, 2020, 59, 1842-1853; and Y. Aoki, L. Li, T. Amari, K. Nishimura and Y. Arashiro, *Macromolecules*, 1999, 32, 1923-1929). Due to its lower gas permeability relative to PET, it is also used in packaging for products that require a strong barrier to $CO_2$ or $O_2$. PEN is also used in copolymerization with PET to improve the mechanical properties of PET, including the glass transition temperature for applications that require polymer rigidity at high temperatures (C.-W. Chen, Y.-H. Yang, S.-C. Lin, S.-P. Rwei and T.-W. Shyr, *Industrial & Engineering Chemistry Research*, 2020, 59, 18717-18725). PEN is also not currently a recycled material.

Based on the ester functionality shared by these polymers and our work on the depolymerization of PET (Z. J. Mast, T. H. T. Myren, C. G. Huntzinger, T. A. Stinson, R. M. Kharbouch, E. M. Almanza, S. E. Zygmont, J. R. Miecznikowski and O. R. Luca, *Inorganic Chemistry Frontiers*, 2020, 7, 1012-1015), this example first describes the chemospecific breakdown of PET, PBT, and PEN using basic hydrolysis focusing on the recovery of monomers from single polymers as well as mixtures. While chemical depolymerization of esters remains an atom-economical approach to break down the macromolecular structures into monomers, the process requires corrosive basic conditions. To address this challenge, we use electrochemistry to generate reactive reagents in situ and therefore avoid the need for high concentration hydroxide in the process. Thus, the goal of this work is three-fold: 1) to increase the applicability of chemical recycling reactions to a wider range of ester plastics including mixtures, 2) to generate products which can be reused as monomer feedstocks, 3) to demonstrate electrochemistry is a method of green, energy-efficient, and cost-effective recycling of mixed polymer waste streams.

Chemical Depolymerization

TABLE 8

Chemical depolymerization reactions for ester polymers.

| Entry | Polymer | Conditions[a] | Temperature (° C.) | % NMR Yield |
|---|---|---|---|---|
| 1 | PET | 0.60 mM | 60 | TPA: 93% |
| 2 | PET | 0.58 mM | 23 | TPA: 66% |
| 3 | PBT | 0.49 mM | 60 | TPA: 44% |
| 4 | PBT | 0.48 mM | 23 | TPA: 28% |
| 5 | PEN | 0.51 mM | 60 | NDA: 41% |
| 6 | PEN | 0.48 mM | 23 | NDA: 16% |
| 7 | Mixture (PBT, PET, PEN) | 0.50 mM PBT, 0.59 mM PEN, 0.60 mM PET in 15 mL | 60 | TPA: 70%[b]; NDA: 31% |
| 8 | Mixture (PBT, PET, PEN) | 0.50 mM PBT, 0.53 mM PEN, 0.61 mM PET | 23 | TPA: 47%[b]; NDA: 15% |

[a]All reactions were run in 15 mL solution of 1:1 water:methanol mixture with 9.38M NaOH and stirring for 87 h. Concentrations estimated for solid suspended in solution based on MW of monomer.
[b]Percent recovery of TPA was calculated using the theoretical monomer expected from both PBT and PET present in the sample.

To identify conditions for the depolymerization of PET, basic conditions were tested at room temperature and 60° C. Gratifyingly, a yield of 93% TPA was obtained at temperature (Table 8 Entry 1) with the room temperature run producing TPA in 66% yield (Table 8 Entry 2). With these conditions in hand, PBT produced yields of 44 and 28% at 60° C. and room temperature respectively (Entries 3 and 4, Table 8). Additionally, PEN was also subjected to the hydrolysis conditions and yields of 41 and 16% NDA were obtained for heated and room temperature reactions (Entries 5 and 6, Table 8). To investigate the mass balance of the PEN depolymerization, we utilized Diffusion Ordered Spectroscopy (DOSY) to assess the presence of oligomers in solution. After workup, the DOSY NMR did not indicate the presence of such oligomers in the medium, thus suggesting a molecular etching mechanism.

Once depolymerizations were confirmed through chemical analyses of recovered monomers, we proceeded to test the reaction conditions on polymer mixtures. We observed recovery of 70% TPA and 31% NDA at 60° C. (Entry 7 Table 8), with the room temperature run giving yields of 47% and 15% for TPA and NDA, respectively (Entry 8 Table 8).

Electrochemical Depolymerization

Scheme 2. Reaction scheme and conditions of PET electrochemical breakdown.

Once the basic hydrolysis results were in hand, we turned to the study of electrochemically-induced depolymerization. We hypothesized that under conditions of reductions of protic media, basic conditions compatible with hydrolysis would be generated. Our work with electrochemical PET depolymerization found that a controlled-potential electrolysis at the solvent window −2.2V vs Ag/AgCl for 1 h, produced modest PET breakdown ~17% in mixed MeOH/water media at carbon electrodes. The addition of heating to 60° C. and stirring for 18 h at the end of the electrolysis produced a TPA yield of 28%. Over the course of this electrolysis, 130 C of charge were passed which would at most account for 0.07 M OH⁻ in the 20 mL working chamber solution. This is a considerably lower amount in comparison to the 9.38 M NaOH used in the previous chemical hydrolysis experiments. Given this observation, it is unlikely that the electrochemical method proceeds through a basic hydrolysis mechanism. This discrepancy led to the hypothesis that the reaction likely proceeds through some short-lived reactive intermediate. Based on this assumption, a series of "cycled" controlled current electrolyses were performed (Table 9). This "cycling" approach consists of applying current, heating, and repeating which allows for the effective generation of reactive species at controlled rates. These species are responsible for the breakdown of the ester bonds and may have limited lifetimes.

TABLE 9

"Cycled"controlled-current electrolysis experiments with PET plastic.

| Entry | Cycle Conditions[a] | Number of Cycles | % Recovery via NMR |
|---|---|---|---|
| 1 | −30 mA for 30 min, 60° C. for 30 min | 3 | 40 |
| 2 | −60 mA for 30 min, 60° C. for 30 min | 4 | 51 |
| 3 | −15 mA for 15 min, 60° C. for 15 min | 4 | 35 |
| 4 | −15 mA for 30 min, 60° C. for 30 min | 4 | 60 |
| 5 | −15 mA for 30 min, 60° C. for 30 min | 6 | 74 |
| 6 | −7.5 mA for 30 mm, 60° C. for 30 min | 6 | 38 |

[a]All experiments run at 0.5 mM concentration of PET. Concentrations estimated for solid suspended in solution based on MW of monomer in 20 mL.

The effects of varying the applied current, the length of cycles, and the number of cycles were studied on PET and the results are summarized in Table 2. Experiments with too high an applied current −60 mA (Entry 2 Table 9) resulted in lower recovery ~51%, likely due to the consumption of the product TPA in undesired side reactions. Too low a current −7.5 mA also produced lower recoveries ~38% (Entry 6, Table 9), suggesting that the amount of charge passed was not sufficient. A controlled current of −15 mA was found to produce the best results across six cycles with 30 min wait times with a high yield of 74%. Four cycles at the same conditions produced only a 60% yield (Entry 4, Table 9).

Once the electrochemical depolymerization of PET had been achieved with good yields, the conditions were applied to a mixture of PET, PBT, and PEN. After six cycles, a 1:1:1 mixture of PET, PEN and PBT produced a 32% yield of 2,6-naphthalene dicarboxylic acid and a 51% yield of terephthalic acid, thus demonstrating the selective breakdown of ester bonds in the electrochemical depolymerization.

Conclusion

We now report that ester polymers can be chemospecifically depolymerized either through a hydrolysis reaction in base in mixed organic/aqueous mixtures at mild temperatures or through the application of cycled controlled-current and mild heating conditions. We have now shown the chemical and electrochemical breakdown of PET, PBT and PEN into their corresponding monomers. Results on the breakdown of mixtures of polymers under mild conditions without corrosive reagents, highlight the potential use of such methods to target specific bonds in mixed materials and bring forth the possibility of single-stream chemical recycling.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A method for electrochemical degradation of a polyester comprising:
   a) providing an electrochemical cell comprising a cathode, wherein the cathode is in electrical communication with a mixture comprising the polyester and an alcoholic solvent;
   b) passing a current through the cathode to form one or more degradation products of the polyester; and
   c) heating the mixture to a temperature ranging from about 40 degrees Celsius to about 80 degrees Celsius following b);
   wherein b) and c) are repeated for one or more cycles.

2. The method of claim 1, wherein the electrochemical cell further comprises an anode, wherein the anode is in electrical communication with the cathode.

3. The method of claim 1, wherein the alcoholic solvent is selected from the group consisting of ethanol, methanol, isopropanol, and tert-butyl alcohol.

4. The method of claim 1, wherein the mixture further comprises water.

5. The method of claim 4, wherein the ratio of the alcoholic solvent to water ranges from about 90:10 to about 10:90.

6. The method of claim 1, wherein the mixture further comprises an electrolyte.

7. The method of claim 6, wherein the electrolyte is selected from the group consisting of an alkali metal halide, an alkali metal nitrate, an alkali metal triflate, an alkylammonium salts, and combinations thereof.

8. The method of claim 6, wherein the electrolyte comprises sodium chloride, potassium chloride, sodium nitrate, sodium triflate, or tetrabutylammonium chloride, or combinations thereof.

9. The method of claim 1, wherein the mixture is heated to a temperature of about 60° C.

10. The method of claim 1, wherein b) and c) are repeated for from one to ten cycles.

11. The method of claim 1, wherein the polyester comprises polyethylene terephthalate (PET).

12. The method of claim 11, wherein the one or more degradation products comprises ethylene glycol and terephthalic acid.

13. The method of claim 1, wherein the polyester comprises polybutylene terephthalate (PBT).

14. The method of claim 13, wherein the one or more degradation products comprises butylene glycol and terephthalic acid.

15. The method of claim 1, wherein the polyester comprises polyethylene naphthalate (PEN).

16. The method of claim 15, wherein the one or more degradation products comprises naphthalene-2,6-dicarboxylic acid and ethylene glycol.

* * * * *